United States Patent [19]

Sonnenberg

[11] Patent Number: 4,535,170
[45] Date of Patent: Aug. 13, 1985

[54] FLAME RETARDANTS AND COMPOSITIONS CONTAINING THEM

[75] Inventor: Joseph Sonnenberg, San Jose, Calif.

[73] Assignee: Raychem Corporation, Menlo Park, Calif.

[21] Appl. No.: 77,494

[22] Filed: Sep. 21, 1980

Related U.S. Application Data

[62] Division of Ser. No. 760,664, Sep. 18, 1968.

[51] Int. Cl.³ .................................. C07D 209/48
[52] U.S. Cl. ........................................ 548/462
[58] Field of Search .............. 260/376 N; 548/462

[56] References Cited

U.S. PATENT DOCUMENTS

| | | | |
|---|---|---|---|
| 2,408,700 | 10/1946 | Sprung | 106/287 |
| 2,547,495 | 3/1951 | Rowland | 260/326 |
| 2,657,169 | 10/1953 | Ligett et al. | 167/33 |
| 3,078,228 | 2/1963 | Smith et al. | 252/33.6 |
| 3,129,225 | 4/1964 | Shapiro et al. | 260/247.2 |
| 3,138,615 | 6/1964 | Bluestane et al. | 260/326 |
| 3,179,632 | 4/1965 | Hendrix | 260/78 |
| 3,208,939 | 9/1965 | Latos et al. | 252/34 |
| 3,275,651 | 9/1966 | Ellis et al. | 260/326 |
| 3,313,763 | 4/1967 | Creighton et al. | 260/41 |
| 3,316,175 | 4/1967 | Latos et al. | 252/32.5 |
| 3,331,797 | 7/1967 | Kopetz | 260/28.5 |
| 3,340,226 | 9/1967 | Stivers | 260/45.75 |
| 3,354,191 | 11/1967 | Stivers | 260/448 |
| 3,382,207 | 5/1968 | Jaquiss | 260/45.7 |
| 3,406,148 | 10/1968 | Sambeth et al. | 260/67 |
| 3,418,263 | 12/1968 | Hindersinn et al. | 260/23 |
| 3,419,576 | 12/1968 | Roberts et al. | 260/326 |
| 3,432,450 | 3/1969 | Jolles | 260/2.5 |
| 3,440,248 | 4/1969 | Roberts et al. | 260/326 |
| 3,455,950 | 7/1969 | Cyba et al. | 260/326 |
| 3,574,230 | 4/1971 | Cyba | 260/326 |
| 3,574,231 | 4/1971 | Gaydasch | 260/326 |
| 3,590,042 | 6/1971 | Cyba | 260/249.6 |
| 3,673,149 | 6/1972 | Gaydasch | 260/45.8 |
| 3,714,151 | 1/1973 | Lyness | 260/240 CA |

FOREIGN PATENT DOCUMENTS

| | | |
|---|---|---|
| 296161 | 12/1965 | Australia . |
| 285913 | 7/1966 | Australia . |
| 409182 | 11/1967 | Australia . |
| 707726 | 12/1967 | Belgium . |
| 664501 | 6/1963 | Canada . |
| 682362 | 3/1964 | Canada . |
| 765828 | 8/1967 | Canada . |
| 787982 | 6/1968 | Canada . |
| 1806584 | 9/1969 | Fed. Rep. of Germany . |
| 1815404 | 6/1970 | Fed. Rep. of Germany . |
| 1259094 | 3/1961 | France . |
| 1470052 | 1/1967 | France . |
| 681054 | 10/1952 | United Kingdom . |
| 928897 | 6/1963 | United Kingdom . |
| 973062 | 10/1964 | United Kingdom . |
| 1004075 | 9/1965 | United Kingdom . |
| 1013786 | 12/1965 | United Kingdom . |
| 1014868 | 9/1966 | United Kingdom . |
| 1064627 | 4/1967 | United Kingdom . |
| 1075420 | 7/1967 | United Kingdom . |
| 1095677 | 12/1967 | United Kingdom . |
| 1100605 | 1/1968 | United Kingdom . |
| 1099096 | 1/1968 | United Kingdom . |
| 1137592 | 12/1968 | United Kingdom . |
| 1145583 | 3/1969 | United Kingdom . |
| 1173943 | 12/1969 | United Kingdom . |
| 1187709 | 3/1970 | United Kingdom . |
| 1191015 | 5/1970 | United Kingdom . |

OTHER PUBLICATIONS

Allen et al., Analytical Chem. 37, 158–159 (1965).
Drew et al., J. Chem. Soc. 1937, pp. 26–33.
Monsanto, Chem. Abs. 68, 59329w (1968).
Journal of the American Chemical Society, vol. 40, pp. 1415–1425 (1918).
Polymer Stabilization, Edited by W. Lincoln Hawkins, Bell Telephone Laboratories, pp. 332–333.
Philippi et al., "Studie uber 1,2–Diaminopropanol und seine Derivate", Annalen der Chemie, 433, 93 (1923).
Simonyi, "Uber die Einwirkung des Hydrazobenzoes Auf Einige Organische Sauren und Saureanhydride", Berichte, 47, 2,569 (1914).
Jacquignon et al., "Les N-Aryltetrachlorophtalimides et Leur Aptitude á la Formation de Complexes Moleculaires", Bull. Soc. Chim. Fr., 935 (1957).
Translation of Japanese Patent Publication No. 3,110/68, dated Feb. 5, 1968.
Translation of "Nihon Kagaku Zasshi", vol. 86, p. 91 (1965).
Translation of "Nan-Nenka to Nan-Nen Zairyo", pp. 87–88, (Mar. 15, 1966).
Translation of "Dai Yuki Kagaku", vol. 4 (1st Edition), p. 83 (Jan. 20, 1959).

Primary Examiner—Donald G. Daus
Assistant Examiner—Mary E. Ceperley
Attorney, Agent, or Firm—Edith A. Rice; Herbert G. Burkard

[57] ABSTRACT

Flame retardants having good stability at the processing temperatures of high melting polymers are described. The flame retardants are halogen-containing bis-imides, for example, those of the formula

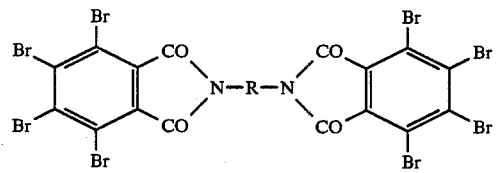

R being defined in the specification.

5 Claims, No Drawings

FLAME RETARDANTS AND COMPOSITIONS CONTAINING THEM

This is a division of application Ser. No. 760,664, filed Sept. 18, 1968.

BACKGROUND OF THE INVENTION

This invention relates to compositions comprising a flammable material and a flame retardant. More especially, it relates to compositions comprising macromolecular flammable materials, for example, polymers. The invention also relates to flame retardants and a process for their manufacture.

The problem of the flammability of certain materials has received considerable attention. One method by which the flammability of certain materials, especially macromolecular materials, has been reduced is by the incorporation therein of halogen-containing compounds, both inorganic and organic. Inorganic halogen-containing compounds often have deleterious effects on the properties of the materials, or damage the equipment in which the materials are processed, because of their corrosive nature, and therefore organic halogen-containing compounds, often in combination with inorganic oxides or non-halogenated salts, have been used most extensively.

While the previously proposed organic halogen-containing compounds have been accepted, many disadvantages are still associated with their use. Many previously proposed flame retardants have been more or less volatile, leading to loss in flame retardance during use of articles containing them, as well as in processing. As macromolecular materials having higher use temperatures (and, accordingly, higher processing temperatures) have been developed, the disadvantages of volatile additives become more marked. In addition, such higher use and processing temperatures have shown up deficiencies in the thermal stability of many of these previously proposed organic halogen-containing flame retardants. Thus, many compounds which have been readily incorporated in materials processed at 150° C. have failed due to volatilization, sublimation or decomposition when incorporated into a material which is processed at temperatures in the region of 250° C. to 350° C. Further, some of the commercial materials are adversely affected by the radiation making them unsuitable for incorporation into compositions which are to be irradiation crosslinked.

Some additives may, for example, be sensitive to water even when incorporated into the material, and when additive-containing compositions are tested with boiling water, the organic compound is dissolved out or hydrolyzed, resulting at best in impaired flame retardance, and often also in corrosion by the hydrolysis products, for example, the halogen acids, resulting from contact with water. Such water sensitivity also shows when the composition is in prolonged contact with a humid atmosphere.

SUMMARY OF THE INVENTION

It is an object of this invention to provide flame retarded compositions which can be processed at elevated temperatures.

It is a further object of the invention to provide a flame retardant having low volatility, good thermal stability and low sensitivity to water.

Other objects of the invention will be apparent from the following description of the invention.

Briefly, the present invention provides a composition comprising a flammable material and a halogen-containing bis-imide. The bis-imides suitable for use in this invention advantageously contain bromine, chlorine, or both of these halogens; bromine-containing compounds are preferred. Advantageously, the halogen atoms are bonded to carbon atoms, the carbon atoms preferably being aromatic carbon atoms, for example, members of a benzene ring.

Advantageously, the bis-imide contains at least 4, preferably at least 8, halogen atoms, preferably at least 4 bromine atoms, which are, as stated above, advantageously bonded to carbon atoms in an aromatic ring. Advantageously, the halogen atoms represent at least about 25% by weight of the molecule.

It will be apparent to those skilled in the art that no precise values for the proportion of the bis-imides in the composition can be given, since this proportion will vary with the particular flammable material, the presence of other additives, the particular bis-imide, and the degree of flame retardance sought in any given application. Further, the proportion necessary to achieve a given extent of flame retardance in a particular composition will depend on the shape of article into which the composition is to be made, for example, electrical insulation, tubing and film will each behave differently. In general, however, the composition may contain from about 5% to about 40%, preferably 20% to 30%, of a bis-imide of the present invention, when the bis-imide is the only flame retardant compound in the composition.

It will be appreciated that one or more bis-imides may be incorporated in the same composition and that other flame retardant materials may be used in conjunction with the bis-imides. It is especially advantageous to use the bis-imide and a compound, especially the oxide, of a Group V element, for example, bismuth, arsenic, phosphorus and especially antimony, in a composition. Of these compounds, antimony oxide is especially preferred. If such a compound is present in a composition, the quantity of bis-imide needed to achieve a given flame-retardance is accordingly reduced.

Accordingly, the present invention also provides a flame retardant system comprising a bis-imide in admixture with a compound of a Group V element, and compositions comprising a flammable material and such a flame-retardant system. The proportions of the bis-imide and the compound are not critical, but in general the bis-imide and the compound are conveniently in a ratio of from about 1:5 to about 15:1, preferably 1:1 to 9:1.

The compositions may contain up to about 40% by weight of the system, preferably between 20% and 30% by weight. It is believed that the inorganic compound and the halogen-containing bis-imide will react under the conditions of combustion of a flammable material to form inorganic halogen compounds, e.g., halides and oxyhalides, which assist in retarding combustion. To the extent that the two components of the system interact, they should be present in approxmately equivalent proportions. The halogen-bearing component also acts as a flame retardant independently and the proportions in a flame retardant system are a matter of choice, depending, inter alia, on the material in which the system is to be incorporated, and commercial considerations. Thus, a mixture in which one component predominates may be regarded as a mixture of equivalent quantities of the two components blended with the one in excess.

The flame retardant bis-imides and systems containing bis-imides may be used in combination with virtually any flammable material. The material may be macromolecular, for example, a cellulosic material or a polymer. Among polymers with which the bis-imide may be combined there may be mentioned, by way of illustrative examples, olefin polymers, for example, homopolymers of ethylene, propylene, butene, copolymers of two or more such monomers and copolymers of one or more such monomers with other copolymerizable monomers, for example, ethylene/propylene copolymers, ethylene/ethyl acrylate copolymers and ethylene/vinyl acetate copolymers; polymers of olefinically unsaturated monomers, for example, polystyrene and styrene copolymers; polyurethanes; polyamides; polyimides; acrylic resins, polyesters, epoxy resins; alkyds; phenolics; elastomers, for example, butadiene/styrene copolymers, butadiene/acrylonitrile copolymers and terpolymers of acrylonitrile, butadiene and styrene; natural rubber; butyl rubber; and polysiloxanes. The composition may contain any of the additives usually present and where appropriate to the particular polymers, may be crosslinked by chemical means or by irradiation.

The bis-imides of the present invention advantageously have one of the following general formulae

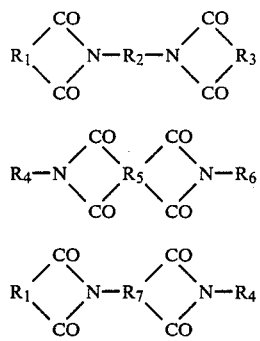

wherein $R_1$, $R_2$ and $R_3$, which may be the same or different, each represent a divalent organic radical, $R_4$ and $R_6$, which may be the same or different, each represent a monovalent organic radical, $R_5$ represents a tetravalent organic radical and $R_7$ represents a trivalent organic radical, and wherein $R_1$, $R_2$ and $R_3$ in Formula I, $R_4$, $R_5$ and $R_6$ in Formula II, and $R_1$, $R_7$ and $R_4$ in Formula III taken together contain at least one halogen atom, preferably at least 4 halogen atoms, advantageously chlorine or bromine atoms, preferably bromine. Advantageously, the halogen atoms represent at least 25% by weight of the molecule and preferably, the halogen atoms are bound to aromatic carbon atoms.

For synthetic reasons, bis-imides of Formulas I and II are preferred, especially Formula I, as are bis-imides in which (in Formula I) $R_1$ and $R_3$ are identical, and (in Formula II) $R_4$ and $R_6$ are identical; it is to be understood, however, that the flame retardant effect of the bis-imides is in no way dependent on their being identical. Furthermore, mixtures of one or more compounds of one or more of each of the above formulae may be employed.

Subject to the requirement that the bis-imides be halogen-containing, radicals $R_1$ to $R_7$ preferably represent radicals such that $R_1(COOH)_2$ and $R_3(COOH)_2$ are each one of the following:
tetrabromophthalic acid
tetrachlorophthalic acid
1,4,5,6,7,7-hexachlorobicyclo-(2.2.1)-5-heptene-2,3-dicarboxylic acid (chlorendic acid)
5,6,7,8,9,9-hexachloro-1,2,3,4,4a,5,8,8a-octahydro-5,8-methano naphthalene-2,3-dicarboxylic acid
5,6,7,8,9,9hexabromo-1,2,3,4,4a,5,8,8a-octahydro-5,8-methano naphthalene-2,3-dicarboxylic acid
phthalic acid
succinic acid
dichloromaleic acid
$R_2(NH_2)_2$ is one of the following:
ethylenediamine
1,6hexamethylenediamine
4,4'-methylenedianiline
4,4'-oxydianiline
phenylenediamines
xylylenediamines
tetrachloroxylylenediamines
tetrabromoxylylenediamines
$R_4NH_2$ and $R_6NH_2$ are one of the following:
2,4,6-trichloroaniline
2,4,6-tribromoaniline
2,3,4,5,6-pentabromobenzylamine
2,3,4,5,6-pentachlorobenzylamine
$R_5(COOH)_4$ is one of the following:
pyromellitic acid
naphthalene-1,4,5,8-tetracarboxylic acid
$R_7(NH_2)(COOH)_2$ is one of the following:
3- or 4-aminophthalic acid
or imide-forming isomers or substitution products of any of the above amines or acids. Further diamines and the dianhydrides of further tetracarboxylic acids are those listed in U.S. Pat. No. 3,179,632, the disclosure of which is incorporated herein by reference.

Thus, the compounds mentioned above may be substituted, or further substituted, by halogen atoms, especially by chlorine or bromine atoms, provided that imides may still be formed therefrom. The compounds may also be substituted by other groups, for example, alkyl, aryl, alkaryl or aralkyl radicals, functional groups and hetero atoms provided that the flame retardant properties of the resulting bis-imides are not adversely affected thereby. It will be appreciated that where water sensitivity is undesirable the bis-imide will not contain groups which would tend to make the bis-imide more water-soluble. It will also be appreciated that the presence of a substituent group on the radical will not in general affect the flame retardant properties except to the extent that the molecular weight is increased. Such an increase in molecular weight would in general mean that a greater weight of bis-imide is necessary to achieve a given degree of flame retardance in a composition; on the other hand, the change in melting point and volatility resulting from the presence of, for example, an additional methyl or ethyl group in the molecule may well be desirable and offset the increase in molecular weight and decrease in proportion of halogen in the molecule.

As illustrative examples of suitable bis-imides, there may be mentioned
N,N'-(p and m-phenylene)-bis[3,4,5,6-tetrachlorophthalimide]
N,N'-(p and m-phenylene)-bis[3,4,5,6-tetrabromophthalimide]

N,N'-(methylene-di-p-phenylene)-bis-[3,4,5,6-tetra-chlorophthalimide]

N,N'-(methylene-di-p-phenylene)-bis[3,4,5,6-tetra-bromophthalimide]

N,N'-(oxy-di-p-phenylene)-bis[3,4,5,6-tetrachlorophthalimide]

N,N'-(oxy-di-p-phenylene)-bis[3,4,5,6-tetrabromophthalimide]

N,N'-(p and m-phenylene)-bischlorendimide

*N,N'-(p and m-tetrachloroxylylene)-bis[3,4,5,6-tetrachlorophthalimide]

*N,N'-(p and m-tetrachloroxylylene)-bis[3,4,5,6-tetrabromophthalimide]

*N,N'-(p and m-tetrachloroxylylene)-bischloroendimide

N,N'-(1,2-ethylene)-bischloroendimide

N,N'-(1,2-ethylene)-bis[3,4,5,6-tetrabromophthalimide]

N,N'-bis(1,2,3,4,5-pentabromobenzyl)-pyromellitimide

N,N'-bis(2,4,6-tribromophenyl)pyromellitimide

*In which the tetrahaloxylylene radicals are 1,2,4,5-tetrahaloxylylene and 1,3,4,5-tetrahaloxylylene radicals.

Certain of these compounds are novel and the present invention accordingly also provides halogen-containing bis-imides (other than those formed from tetrachlorophthalic anhydride and p,p'-diaminodiphenylmethane and 2,4-diaminotoluene), especially compounds of the formula

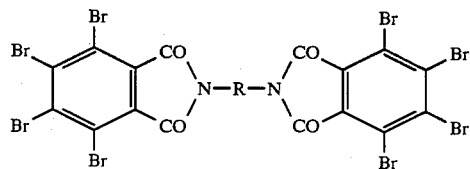

or

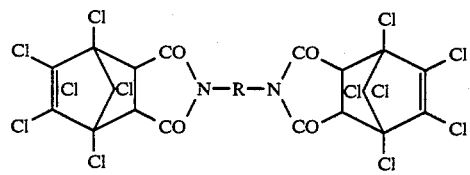

in which R represents a divalent aliphatic, aromatic or araliphatic radical which may be substituted by one or more halogen atoms or interrupted by hetero atoms. Preferably R, when it is an aliphatic radical, is an alkylene radical and preferably it contains from 1 to 18 carbon atoms, especially from 2 to 10 carbon atoms. When R is an aromatic radical, it may contain 1, 2 or more ring systems which may be joined, when there are two or more, by aliphatic radicals, by hetero atoms, especially oxygen, or directly; the imide nitrogen atoms may be bonded directly to the aromatic system or by an alkylene chain. The aromatic rings may advantageously be substituted by one or more halogen atoms, preferably by bromine and especially by chlorine atoms.

More especially, the present invention provides compounds of the Formula IV in which R represents a radical of the formula

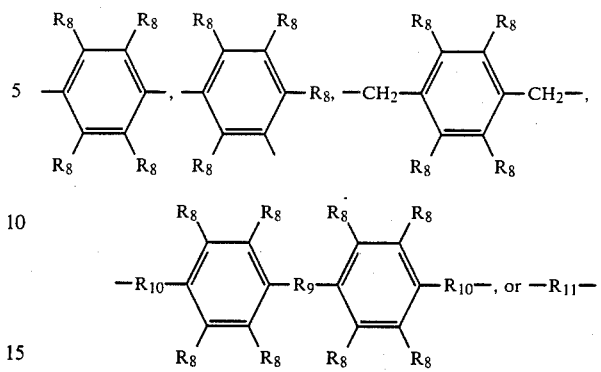

in which each $R_8$, which may be the same or different, represents hydrogen, an alkyl radical containing from 1 to 4 carbon atoms, or a halogen atom, $R_9$ represents an alkylene radical, preferably containing 1 carbon atom, or hetero atom or group, preferably oxygen, or is absent, $R_{10}$ represents an alkylene radical having from 1 to 4 carbon atoms or is absent, and $R_{11}$ represents an alkylene radical having from 1 to 18, preferably 2 to 10, carbon atoms.

The bis-imides may be made by any of the methods in general use or described in the literature for the manufacture of imides. In general, the imide results from heating together the corresponding anhydride and amine with elimination of water, the reactants being dissolved in a common solvent. Suitable solvents include, for example, N-methyl-2-pyrrolidone, dimethylacetamide, xylene and cresol.

Generally, the imide will be precipitated from the solution either during the reaction or on cooling after reaction. If the imide is required pure, the precipitate may be filtered, washed, and recrystallized from a suitable solvent.

The bis-imides may be incorporated with the flammable material by any of the methods normally employed for the admixture of additives to the material. For example, when the flammable material is a polymer, the bis-imides, which are solid at room temperature and may generally be obtained in the form of powders, may be blended with granules, pellets, chips or a powder of the polymer in a tumbler or milled into a composition of the polymer and additives.

The invention will now be illustrated in the following examples, in which all parts are by weight unless otherwise indicated.

EXAMPLE 1

Preparation of N,N'-(2,4,5,6-tetrachloro-m-xylylene)-bischlorendimide

A 1 liter flask was equipped with a nitrogen purge, a heating mantle, a mechanical stirrer, a reflux condenser and a Dean-Stark apparatus (a graduated vessel which allows the volume of water in the condensate to be measured). To 81.6 gms (0.22 mole) of 1,4,5,6,7,7-hexachlorobicyclo-(2.2.1)-5-heptene-2,3-dicarboxylic anhydride (chlorendic anhydride) was added 27.4 gms (0.1 mole) of 2,4,5,6-tetrachloro-m-xylylenediamine in 500 ml. xylene. The mixture was refluxed (at about 140° C.) for 2 hours, after which the reaction mixture was a clear solution, 3.2 ml. of water having been collected in the Dean-Stark apparatus. The solvent was then boiled off, precipitation occurring when about 450 ml. of xylene had been removed. The remaining slurry was cooled and filtered to yield fine white crystals which were washed with methanol. Addition of methanol to the filtrate yielded a second crystalline precipitate; the infrared (IR) spectra of the two compounds were identical. The first compound (62.1 gms) had a melting point of 293°–206° C., the second compound (6.9 gms) melted at 285°–290° C., indicating a lower purity. The IR spectrum was indicative of an imide and showed no amide absorption. The total yield was 68%.

| Analysis: $C_{26}H_8Cl_{16}N_2O_4$ | | |
|---|---|---|
| | Calc. % | Found % |
| Carbon | 31.9 | 31.8 |
| Hydrogen | 0.8 | 1.3 |
| Nitrogen | 2.9 | 3.0 |
| Chlorine | 57.9 | 58.3 |

EXAMPLE 2

Preparation of N,N'-(p-phenylene)-bis[3,4,5,6-tetrachlorophthalimide]

In a 5 liter round-bottom flask equipped with a heating mantle, a stirrer, a thermometer, a condenser and a nitrogen purge, there were reacted 457.5 gms (1.6 mole) of tetrachlorophthalic anhydride and 86.5 gms (0.8 mole) of p-phenylenediamine in 2000 ml. of N-methyl-2-pyrrolidone (NMP), the reactants going into solution as the mixture was heated with stirring. At 170° C., precipitation began and continued as the temperature was raised to 200° C. where it was maintained for 90 minutes. The reaction mixture was then allowed to cool overnight. The cooled mixture was filtered and the yellow precipitate was recovered. The precipitate was washed with NMP, thoroughly stirred in acetone, filtered and washed with more acetone. The product was dried under vacuum at 150° C. for 16 hours. 272.7 gms (yield=53%) of an ivory-yellow material was obtained, having a melting point in excess of 500° C., with some sublimation at about 425° C. The IR spectrum had the characteristics of an imide with the absorption bands at 1710s and 1770w cm$^{-1}$. The product was insoluble in water.

| Analysis: $C_{22}H_4Cl_8N_2O_4$ | | |
|---|---|---|
| | Calc. % | Found % |
| Carbon | 41.0 | 41.5 |
| Hydrogen | 0.6 | 0.7 |
| Nitrogen | 4.4 | 4.5 |

| -continued | | |
|---|---|---|
| Analysis: $C_{22}H_4Cl_8N_2O_4$ | | |
| | Calc. % | Found % |
| Chlorine | 44.0 | 44.7 |

EXAMPLE 3

Preparation of N,N'-(p-phenylene)-bis[3,4,5,6-tetrabromophthalimide]

108 gms (1.0 mole) of p-phenylenediamine was dissolved in 1 liter of warm NMP under a nitrogen atmosphere and the solution filtered to remove suspended particles. This filtered solution was then added to a similarly prepared filtered solution of 928 gms (2.0 moles) of tetrabromophthalic anhydride in 2 liters of warm NMP in the apparatus described in Example 2. A mildly exothermic reaction took place and the mixture was further heated while stirring. At about 145° C., precipitation began. The quantity of brown precipitate increased with continued heating and a further 2 liters of NMP was added to facilitate stirring, the temperature being raised to 200° C. and maintained for 2 hours, before the mixture was allowed to cool. The precipitate was collected, washed with NMP, roughly dried and washed with acetone. The material was then stirred well with acetone, filtered and again washed before being dried overnight at 150° C. under vacuum. The product was a fine, rusty-gold precipitate with a melting point above 500° C. The yield was 486 gms (49%), the infrared spectrum having the characteristic imide structure, absorption bands at 1712s and 1765w cm$^{-1}$. The compound was insoluble in water, methanol, ether, xylene, dimethyl sulphoxide and dimethyl acetamide.

| Analysis: $C_{22}H_4Br_8N_2O_4$ | | |
|---|---|---|
| | Calc. % | Found % |
| Carbon | 26.4 | 26.7 |
| Hydrogen | 0.4 | 0.5 |
| Nitrogen | 2.8 | 2.9 |
| Bromine | 64.0 | 63.2 |

The nonvolatility of the product was demonstrated by subjecting the product to a vacuum ($1 \times 10^{-6}$ torr.) at a temperature of 300° C. and analyzing the gas in contact with the product by mass spectrography. No trace of the product in the gas was found.

EXAMPLES 4 TO 22

The following compounds were prepared under conditions generally similar to those of Example 1, 2 or 3.

TABLE 1

| Ex. No. | Bis-Imide From: | Time Hrs. | Temp. °C. | Solvent | Product Character | Yield % | Mp °C. |
|---|---|---|---|---|---|---|---|
| 4 | Chlorendic anhydride and MPD | 1 | 120 | Xylene | Fine white crystals | 85 | 342–45 |
| 5 | Chlorendic anhydride and PPD | 1.5 | 140 | Xylene | Lavender precipitate | 71 | >475 |
| 6 | Chlorendic anhydride and PXD | 0.5 | 140 | Xylene | White precipitate | 88 | 328–30 |
| 7 | Chlorendic anhydride and ND | 0.5 | 125 | Xylene | White crystals | 68 | 354–56 |
| 8 | Tetrachlorophthalic anhydride and MPD | 0.5 | 140 | Xylene | Yellow precipitate | 95 | 405 |
| 9 | Tetrachlorophthalic anhydride and MXD | 1.0 | 195 | NMP | Yellow precipitate | 33 | 400–10 |
| 10 | Tetrachlorophthalic | 2.5 | 200 | NMP | Yellow | 19 | 465 dec |

TABLE 1-continued

| Ex. No. | Bis-Imide From: | Time Hrs. | Temp. °C. | Solvent | Product Character | Yield % | Mp °C. |
|---|---|---|---|---|---|---|---|
|  | anhydride and PXD |  |  |  | precipitate |  |  |
| 11 | Tetrabromophthalic anhydride and MPD | 2.5 | 200 | NMP | Fluffy yellow precipitate | 44 | 454–58 |
| 12 | Tetrabromophthalic anhydride and MXD | 0.5 | 175 | NMP | Ivory precipitate | 57 | 445 |
| 13 | Tetrabromophthalic anhydride and PXD | 2.5 | 200 | NMP | Yellow ivory precipitate | 18 | 436–40 |
| 14 | Tetrabromophthalic anhydride and MD | 2.5 | 200 | NMP | Yellow precipitate | 57 | 390–95 |
| 15 | Tetrabromophthalic anhydride and OD | 2.5 | 200 | NMP | Yellow precipitate | 29 | 410–15 |
| 16 | Tetrabromophthalic anhydride and ED | 0.5 | 200 | NMP | Yellow precipitate | 26 | 465 dec |
| 17 | Tetrachlorophthalic anhydride and MD | 0.5 | 175 | NMP | Light yellow precipitate | 58 | 367–70 |
| 18 | Tetrachlorophthalic anhydride and OD | 0.5 | 160 | DMA | Yellowish precipitate | 44 | 380–83 |
| 19 | Phthalic anhydride and MXD | 1.0 | 180 | NMP | Fine white crystals | 86 | 285–87 |
| 20 | Chloran and PPD | 0.5 | 135 | Xylene | Lavender precipitate | 45 | 400 dec |
| 21 | Chloran and PXD | 1.0 | 180 | NMP | Off-white powder | 83 | 410 dec |
| 22 | Pyromellitic dianhydride and pentabromobenzyl- amine | 17.0 | 200 | NMP | White powder | 91 | >500 |

Where:
ED represents ethylenediamine
MD represents 4,4'-methylenedianiline
OD represents 4,4'-oxydianiline
MPD represents m-phenylenediamine
PPD represents p-phenylenediamine
MXD represents 2,4,5,6-tetrachloro-m-xylylenediamine
PXD represents 2,3,5,6-tetrachloro-p-xylylenediamine
NMP represents N-methyl-2-pyrrolidone
DMA represents N,N'-dimethylacetamide
Chloran represents 2,3-dicarboxy-5,8-endomethylene-5,6,7,8,9,9-hexachloro-1,2,3,4,4a,5,8,8a-octahydronaphthalene anhydride

EXAMPLE 23

Preparation of p-(3,4,5,6-tetrabromophthalimide)-p'-(3,4,5,6-tetrachlorophthalimide)-diphenylmethane A heated solution of 13.24 gms (0.046 mole) of 3,4,5,6-tetrachlorophthalic anhydride in 25 ml. xylene was added to a heated solution of (26 gms, 0.041 mole) p-amino-p'-(3,4,5,6-tetrabromophthalimide)-diphenylmethane in 425 ml. xylene and the mixture refluxed for 4.5 hours. A yellow precipitate was filtered from the hot reaction mixture, washed in turn with hot xylene and methanol and dried under vacuum at 100° C. The yield was 7.7 gms (21%). After two recrystallizations from dimethylacetamide and methanol, the melting point was 383° C., with decomposition.

The p-amino-p'-(3,4,5,6-tetrabromophthalimide)diphenylmethane was prepared as follows: 148.5 gms (0.25 mole) of 4,4'-methylenedianiline was dissolved in 400 ml. of hot xylene, 115.7 gms (0.25 mole) of 3,4,5,6-tetrabromophthalic anhydride was dissolved in a second sample of hot xylene and the two solutions mixed, stirred under reflux for 2 hours, and allowed to stand overnight. The mixture was then reheated to boiling, the remaining solid filtered, washed with xylene and methanol, and dried at 100° C. under vacuum. Recrystallization from xylene gave dark orange crystals. On heating the solid, it darkens at 240° C., decomposition appearing complete at 340° C. Infrared analysis shows bands corresponding to $NH_2$ (3450 and 1628 $cm^{-1}$) and imide (1720 and 1765 $cm^{-1}$) groups.

EXAMPLE 24

Preparation of N,N'-(2,3,5,6-tetrachloro-p-xylylene)-bisphthalimide

In a 3 liter, round-bottom flask equipped with a heating mantle, mechanical stirrer, thermometer, nitrogen inlet and condenser, 137 gms (0.5 mole) of 2,3,5,6-tetrachloro-p-xylylenediamine was dissolved at room temperature in 1 liter N-methyl-2-pyrrolidone (NMP). While stirring, 150 gms (1.0 mole) solid phthalic anhydride was added, the temperature rising to 47° C. The resulting greenish solution was heated to 180°–185° C. for 30 minutes, after which period crystallization took place. The hot mixture was poured into a 2 liter beaker when mass crystallization occurred.

After cooling to room temperature, the tan crystalline mass was filtered, washed with NMP, slurried with acetone and refiltered. After partial air drying, the crystals were dried in a vacuum oven for 2.5 hours at 110° C. Yield was 227.9 gms (85%), melting point, 328°–330° C.

| Analysis: $C_{24}H_{12}Cl_4N_2O_4$ | | |
|---|---|---|
|  | Calc. % | Found % |
| Carbon | 53.88 | 54.64 |
| Hydrogen | 2.41 | 2.30 |
| Nitrogen | 5.24 | 5.41 |
| Chlorine | 26.51 | 26.51 |

In the following examples, the symbols have the following meanings:
A = perchloropentacyclo[5.2.1.0$^{2,6}$.0$^{3,9}$.0$^{5,8}$]decane
B = 1,4,7,10-dimethanocycloocta-1,2,3,4,7,8,9,10,13,13,14,14-dodecachloro-1,4,4a,5,6,6a,7,10,10a,11,12,12a-dodecahydro[1,2,5,6]dibenzene
Example 1, etc. = product of Example No. 1, etc.

EXAMPLE 25

Compounds of the invention were blended with poly(1,12-dodecamethylene pyromellitimide) and produced as described in a copending application filed on even date with this application by Edward C. Stivers entitled "Polymers, Process and Articles", the disclosure of which is incorporated herein by reference. This is a high-melting polymer which is processed at temperatures in excess of 300° C., a temperature at which many flame retardants decompose. Compositions containing the polymer, 2% Irganox 1010 (an anti-oxidant-pentaerythritol tetra-3,5-ditert.butyl-4-hydroxydihydrocinnamate) and a compound of the invention were pressed into slabs of dimensions 4.0"×0.25"×0.05" at 330° C. and tested according to ASTM D635-63, but modified to test 4 strips of each composition having the given dimensions. This test, in which a Bunsen flame is contacted with one end of the strip, is used to compare the flammability of different materials. A short time to self-extinction, or a small extent or rate of burning, indicates good flame retardant properties.

TABLE II

| Additive | Additive PHR | $Sb_2O_3$ PHR | Aver. Sec. to Self-Extinction | Dripping |
|---|---|---|---|---|
| 0 | 0 | 0 | Burnt | Yes |
| Example 2 | 20 | 10 | 5 | No |
| Example 2 | 30 | 15 | 0 | No |
| Example 3 | 25 | 0 | 1 | No |
| Example 22 | 25 | 0 | 2 | No |
| Example 24 | 30 | 16 | 2 | No |

A similar slab containing 20 PHR of compound B was also prepared. This slab was black, indicating considerable decomposition of the commercial flame retardant.

EXAMPLE 26

Various compositions of low density polyethylene containing no flame retardant, commercially available flame retardants and the flame retardants of the present invention were prepared. The flammability of slabs 0.060" thick prepared from the compositions was measured according to ASTM D635-63, but modified to test 4 samples of each composition.

TABLE III

| Run No. | Additive | Additive PHR | $Sb_2O_3$ PHR | Average Burning Extent (in.) | Rate (in./min.) |
|---|---|---|---|---|---|
| 1 | 0 | 0 | 0 | 3.00 | 1.24 |
| 2 | A | 10 | 20 | 2.65 | 1.06 |
| 3 | A | 20 | 10 | 3.00 | 0.84 |
| 4 | B | 10 | 20 | 2.45 | 0.93 |
| 5 | B | 15 | 15 | 1.32 | 0.75 |
| 6 | B | 20 | 10 | 0.25 | 0.55 |
| 7 | B | 30 | 0 | 3.00 | 0.89 |
| 8 | Ex. 1 | 10 | 20 | 2.00 | 0.72 |
| 9 | Ex. 1 | 20 | 10 | 0.45 | 0.53 |
| 10 | Ex. 3 | 15 | 15 | 0.90 | 0.84 |
| 11 | Ex. 3 | 20 | 10 | 0.25 | 0.36 |
| 12 | Ex. 3 | 25 | 5 | 0.05 | 0.27 |
| 13 | Ex. 3 | 27 | 3 | 0.40 | 0.32 |
| 14 | Ex. 3 | 28 | 2 | 0.50 | 0.49 |
| 15 | Ex. 3 | 30 | 0 | 0.98 | 0.47 |
| 16 | Ex. 16 | 20 | 10 | 0.10 | 0.55* |
| 17 | Ex. 3 | 20 | 10 | 0.30 | 0.47* |

*These samples contained 0.3 parts per hundred resin of Santonox R [4,4'-thiobis(6-tert-butyl-m-cresol)].

The reduction in both the rate and extent of burning compared with compositions containing no flame retardant and commercially available flame retardants can be seen. There was no dripping from any sample containing a flame retardant.

EXAMPLE 27

The following compositions were prepared and formed into slabs 0.060" thick.

| | Parts by Weight |
|---|---|
| Polyethylene (low density DFD 6040) | 100 |
| 2-hydroxy 4-n-octoxybenzophenone (Cyosorb UV 531 light absorber) | 0.1 |
| 4,4'-thiobis(6-tert-butyl-m-cresol) (Santonox R) | 0.1 |
| Flame retardant | See Table IV |

50% of the slabs were irradiated to a dose of 15 Mrad from each side. All slabs were tested as in Example 26.

TABLE IV

| Run No. | Additive | Additive PHR | $Sb_2O_3$ PHR | Average Burning Extent (in.) | Rate (in./min.) |
|---|---|---|---|---|---|
| | Unirradiated | | | | |
| 1 | 0 | 0 | 0 | 3.00 | 1.54** |
| 2 | B | 20 | 10 | 0.75 | 0.43 |
| 3 | B | 30 | 0 | 3.00 | 1.02 |
| 4 | Ex. 3 | 20 | 10 | 0.38 | 0.66 |
| 5 | Ex. 3 | 30 | 0 | 0.32 | 0.62 |
| | Irradiated | | | | |
| 6 | 0 | 0 | 0 | 3.00 | 1.89** |
| 7 | B | 20 | 10 | 2.40 | 0.63 |
| 8 | B | 30 | 0 | 3.00 | 1.14* |
| 9 | Ex. 3 | 20 | 10 | 0.82 | 0.41 |
| 10 | Ex. 3 | 30 | 0 | 0.38 | 0.76* |

**In these tests, dripping of melted material took place.
*In these tests, there was slight dripping of melted material.

Table IV shows the superiority of the flame retardant of the present invention, especially in the irradiated polyethylene. It will be noted also that the flame retardant of the present invention is effective in reducing the rate and extent of burning in the absence of any antimony oxide or similar additive.

EXAMPLE 28

The product of Example 14 was incorporaed into an acrylonitrile-butadiene-styrene polymer (CYCLOLAC X-27, made by Marbon Chemical, Division of Borg-Warner Corporation), and slabs of dimensions 5.0"×0.5"×0.06" were tested according to ASTM D635-63, modified to test four samples.

TABLE V

| Additive | Additive PHR | $Sb_2O_3$ PHR | Results |
|---|---|---|---|
| 0 | 0 | 0 | Burnt at 2.3"/min. |
| Ex. 14 | 25 | 12.5 | Non-burning; 3-5 sec. afterglow |

EXAMPLE 29

Two compounds of the invention were incorporated into polypropylene (Shell W550, a polymer stated to be especially suitable for articles which will be exposed to elevated temperatures), the composition was pressed into slabs 5.0"×0.5"×0.06", and tested according to ASTM D635-63.

TABLE VI

| Additive | Additive PHR | Sb$_2$O$_3$ PHR | Average Burning | | Dripping |
|---|---|---|---|---|---|
| | | | Extent (in.) | Rate (in./min.) | |
| 0 | 0 | 0 | | 1.2 | Yes |
| Ex. 14 | 26.7 | 13.3 | 0.3 | | No |
| Ex. 1 | 20 | 10 | 0.8 | | Slight |

In general, those compounds of the present invention containing bromine atoms bound to aromatic carbon atoms have higher flame retardance and lower thermal stability than a corresponding compound containing chlorine atoms. It is also believed that in general the thermal stability of a compound containing a halogen atom bound to an aliphatic carbon atom is lower than that of a similar compound containing the same halogen atom bound to an aromatic carbon atom. These differences enable the user to choose a compound of the invention suitable for a particular purpose. The compounds of this invention can be processed at temperatures which will cause the decomposition of many commercially available materials.

It is believed that the stability of the compounds of this invention at processing temperatures of polymer materials is in part due to their being solid at these temperatures, and accordingly those compounds having melting points in excess of about 275° C. are preferred.

It is to be understood that all halogen-containing bis-imides are the subject of this invention, and that the foregoing examples are intended to be by way of illustration only and that the compounds of the invention can be used to flame retard a variety of materials other than the polymers hereinbefore described, these compositions indicating only some exemplary compositions in which the bis-imides have been found especially effective. It is also clearly to be understood that mixtures of two or more bis-imides may be employed when practicing this invention. The bis-imides can be combined with the materials commonly used or proposed for use as flame retardant synergists without departing from the ambit of the invention. Thus, the invention is to be regarded as limited only by the lawful scope of the appended claims.

I claim:

1. A bisimide compound of the formula

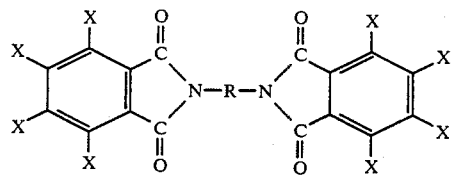

wherein each X is independently bromine or hydrogen with the proviso that at least 4 of said X's are bromine, and R represents an alkylene radical of 2 to 18 carbon atoms.

2. A bisimide as claimed in claim 1 in which each said X is bromine.

3. A bisimide as claimed in claim 2 in which R is an alkylene radical of 2 to 6 carbon atoms.

4. A bisimide as claimed in claim 3 which is N,N'-(1,2-ethylene)-bis[3,4,5,6-tetrabromophthalimide].

5. A bisimide as claimed in claim 3 which is N,N'-(1,4-tetramethylene)-bis[3,4,5,6-tetrabromophthalimide].

* * * * *